United States Patent [19]

Scoates

[11] 4,329,649
[45] May 11, 1982

[54] ION SENSOR PROBE

[75] Inventor: Kenneth D. Scoates, Pittsburgh, Pa.

[73] Assignee: Gibbs & Hill, Inc., New York, N.Y.

[21] Appl. No.: 102,930

[22] Filed: Dec. 12, 1979

[51] Int. Cl.³ .......................................... G01N 27/42
[52] U.S. Cl. ................................................. 324/438
[58] Field of Search .................... 324/438; 204/195 F

[56] References Cited

U.S. PATENT DOCUMENTS

| | | |
|---|---|---|
| 3,350,636 | 10/1967 | Winsel ................................. 324/438 |
| 3,355,375 | 11/1967 | Badgley ............................. 324/438 |
| 4,151,255 | 4/1979 | Capuano et al. .................... 324/438 |
| 4,169,125 | 9/1979 | Rodriguez et al. . | |

Primary Examiner—Michael J. Tokar
Attorney, Agent, or Firm—Pennie & Edmonds

[57] ABSTRACT

An ion sensor probe for constant monitoring of the pH level of a solution in a scrubbing system. The probe includes a tubular housing having a plug member inserted at one end thereof. The plug member supports an ion sensor cell and a reference cell in a side-by-side relationship. Each of the cells has one end exposed for contacting the solution. The plug member encloses the one end of the ion sensor cell to form a chamber which communicates with a bore in the plug member. A cleaning fluid of water and an acidic solution can be independently admitted into the chamber to cleanse the one end of the ion sensor cell. The probe is inserted into a well member shaped to receive the probe and having one end configured so as to permit only a portion of the solution to contact the ion sensor cell.

16 Claims, 3 Drawing Figures

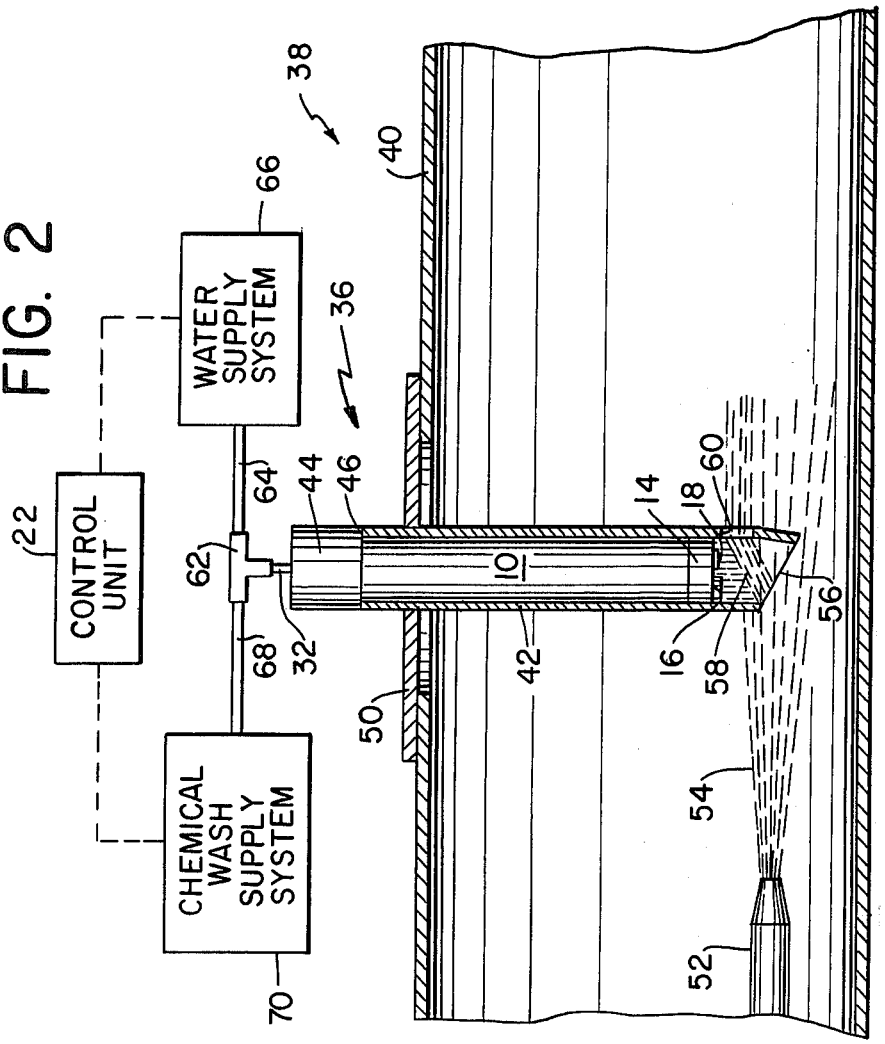

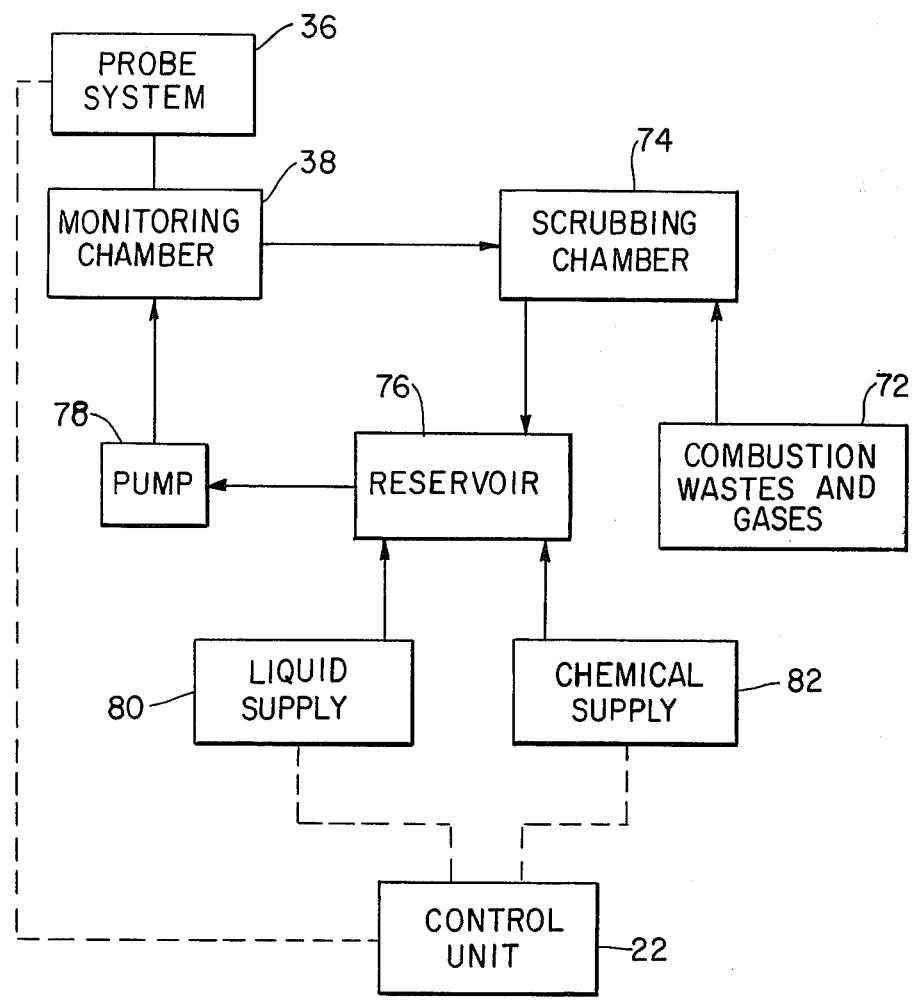

ION SENSOR PROBE

TECHNICAL FIELD

This invention relates to a sensing device and in particular to a self-cleaning ion sensor probe for monitoring the pH level of an aqueous solution which is admitted into a scrubber chamber so as to wet the particulates and chemically react with the gases therein.

BACKGROUND ART

In scrubbing systems it is necessary to regulate the pH of an aqueous solution therein during their operation. Such systems are typically employed with fossil-fueled electrical generating plant in which particulates and waste gases generated during combustion are removed by a wet-gas scrubbing process in a scrubber chamber. This process involves the injection of a liquid such as water into the scrubber chamber so as to wet the particulates therein. The liquid adds appreciably to the weight of the particulates and causes them to fall countercurrent to the stream of gases. In addition, the liquid is chemically treated to form a solution which chemically reacts and neutralizes the waste gases generated. The amount of chemical added to the liquid is dependent upon the pH level necessary to provide the chemical activity desired. Since the solution admitted into the scrubber chamber is usually recycled, a reliable monitoring system is necessary to constantly transmit the pH of the solution to a control unit. In this manner, the control mechanisms can be operated properly to regulate the pH by varying the chemical content of the solution.

Typically, the monitoring system includes an ion sensor and a reference cell which are exposed to the solution to be monitored. However, as a result of the extreme environment to which the ion sensor is exposed, the ion sensor has a limited lifetime. In particular, the erosion, corrosion, and build-up of particulates to which the sensor unit is subjected severely limits the operation as well as the useful duration of the sensor unit. As a result, the ion sensor requires continuous supervision to assure its proper functioning. This supervision includes frequent physical removal of the ion sensor and cleaning of the build-up of deposits and the scored or scaled surface of the ion sensor as well. In addition, frequent replacement of the ion sensor is required due to wear and tear from the extreme environment to which it is exposed. Such supervision not only increases the operational cost of the system but also degrades the performance as well.

Applicant has invented an improved ion sensor probe which overcomes the above-noted limitations of the prior art.

DISCLOSURE OF INVENTION

In accordance with the present invention, a probe for monitoring the pH of a solution comprises at least one sensor cell and housing means for supporting the sensor cell having one end available for exposure to the solution. The probe also comprises means for cleansing the one end of the sensor cell.

In a preferred embodiment, an ion sensor probe comprises at least one ion sensor cell and at least one reference cell. A housing means is provided for supporting the ion sensor cell and the reference cell, each of which has one end available for exposure to the solution. The probe also comprises means for passing a cleansing fluid over the one end of the ion sensor cell. Preferably the housing means defines a chamber enclosing the one end of the ion sensor cell. The chamber has at least one opening so as to permit the ion sensor probe to come into contact with the solution.

The present invention also relates to an ion sensor probe system for monitoring the pH of a portion of an aqueous solution or a slurry stream flowing in a conduit having an opening at a surface portion therof. The system comprises an ion sensor probe substantially as described above for monitoring the pH of a portion of the slurry system. The system also comprises a well member extending through the opening and shaped to receive the ion sensor probe therein. One end of the well member extends beyond the one end of the ion sensor cell and defines an enclosure configured so as to permit at least a portion of the slurry stream to contact the one end of the ion sensor cell. Preferably the enclosure has an inlet and an outlet disposed below the one end of the ion sensor cell. Also, the inlet is disposed below the outlet. The outlet is smaller than the inlet so as to provide a pressure buildup within the enclosure whereby the entering solution will substantially fill the enclosure in a spray form and contact the ion sensor cell.

BRIEF DESCRIPTION OF DRAWINGS

The present invention is described in detail below with reference to the drawings in which:

FIG. 2 is a side cross-sectional view of an ion probe system according to the present invention and including the self-cleaning ion probe of FIG. 1.

FIG. 3 is a schematic view of the ion probe system of FIG. 2 in a scrubbing system according to the present invention.

BEST MODE FOR CARRYING OUT THE INVENTION

Figure 1:
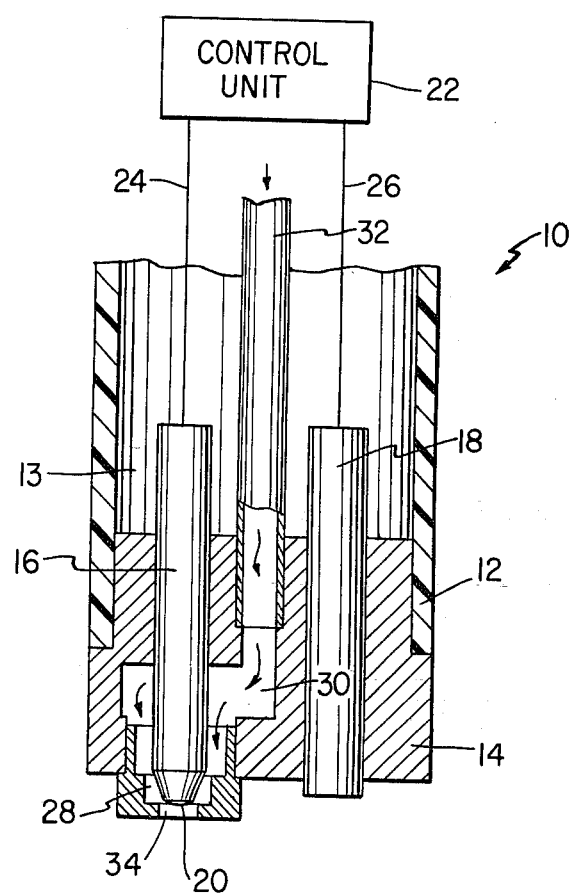
FIG. 1 is a side cross-sectional view of a self-cleaning ion probe according to the present invention.

Referring to the FIGS., a self-cleaning ion sensor probe 10 includes a housing 12 preferably constructed of polyvinylchloride (PVC) which has at least one open end 13. A plug 14 is shaped to permit easy insertion into and retention in the open end of the housing 12. The plug 14 has a first and a second passageway for receiving an ion sensor cell 16 and a reference cell 18 in a side-by-side relationship. The ion sensor cell 16 has a glass surface 20 at the lower end thereof. The ion sensor cell 16 and reference cell 18 are coupled to a control unit 22, to be explained more fully below, by means of electrical connections 24, 26 respectively. The type of ion sensor used will depend on the specific ion to be monitored.

In a preferred embodiment for use with the scrubbing system described below, the ion sensor cell 16 is a silver/silver chloride sensor having, as indicated above, a glass surface 20. Also according to the preferred embodiment, the reference cell 18 is a potassium chloride silver/silver chloride cell which normally does not require any washing. Both the sensor cell 16 and reference cell 18 are coupled to a voltage source with the ion sensor 16 developing a voltage and the reference cell 18 providing a return path of current. The signal developed by the probe 10 is fed to the control unit 22 where it can be amplified and measured for display purposes or employed as a control signal for further operations.

The plug member 14 also includes a flush chamber 28 which circumferentially encloses the lower end of the ion sensor cell 16 and thereby the glass surface 20. The flush chamber 28 communicates with a passageway 30 which in turn communicates with one end of a flush tube 32 extending into the passageway 30. The diametral dimension of the outlet opening 34 of flush chamber 28 is less than that within the flush chamber 28. This provides that any fluid entering the flush chamber 28 will completely fill the chamber 28 and thereby totally wash the lower end of the ion sensor cell 16.

The probe 10 can be incorporated in a probe system 36 for use in a monitoring chamber 38 shown as a conduit 40 in FIG. 2 and schematically in FIG. 3.

The probe system 36 in addition to the probe 10 includes a well 42 which is configured to receive the probe 10. Both the exterior of the probe 10 and the interior of well 42 could be of any desired shape, i.e., circular or rectangular, provided that the probe 10 can be inserted within the well 42. Preferably the probe 10 and well 42 have compatible shapes so as to permit a secure fit of the probe 10 within well 42. The upper portion 44 of the probe 10 has shoulders 46 which rest upon a flange 48 on the well 42. The shoulders are positioned so that the probe 10 extends a desired distance into the well 42. The probe well 42 extends perpendicularly into the conduit 40 through a manhole 50 which covers an opening in a surface of the conduit 40.

The lower end of the well 42 is positioned adjacent the discharge end of a nozzle 52 for producing a spray 54 of an aqueous solution or a slurry stream in the axial direction of the chamber 40 as more fully described below. The lower end of the well 42 has an inlet opening 56 which is oblique to the direction to the spray 54. The lower end of well 42 also defines a flow chamber 58 in which a portion of the spray 54 is captured and permitted to contact the lower end of the ion sensor cell 16 within the flush chamber 28. On the downstream side of the well 42 is an outlet opening 60 which permits the portion of the spray 54 entering the flow chamber 58 to exit therefrom. The outlet opening 60 is smaller in dimension than the inlet opening 56 so as to provide a pressure buildup of the portion of the spray 54 within the flow chamber 58. This assures that the portion of the spray 54 within the flow chamber 58 will rise to contact the ion sensor cell 16 and reference cell 18 which need only to be slightly wetted by the spray 54 in order to permit measurement of the pH level of the aqueous solution.

The configuration of the flow chamber 58 permits not only the control of the flow and velocity of the spray 54 over the ion sensor cell 16 but also protects the ion sensor cell 16 against any direct contact with solid particulates carried with the spray 54. This greatly aids in prolonging the useful life of the ion sensor unit 16.

At the upper end of the probe 10, the flush tube 32 extends to a T-fitting 62. One inlet of the T-fitting 62 is connected by tube 64 to a water supply system 66 which provides water preferably pressurized at 80 pounds per square inch (PSI). The T-fitting is also connected through a tube 68 to a chemical wash supply system 70 which provides either an acidic or a caustic solution depending on the pH value of the spray 54. Both the water supply system 66 and the chemical wash supply system 70 have valves which are regulated by the control unit 22 as indicated by the dashed lines. The control unit 22 includes a timer control operative to periodically regulate the respective valves and thereby discharge either the water or chemical wash through the respective connections to the flush chamber 28. In this manner, the ion sensor cell 16 is washed at required time intervals. The conduit 40 or monitoring chamber 38 are normally operating at subatmospheric pressure. Therefore the chemical or water wash supply systems 66, 70 need not be pressurized since the wash materials will be drawn into the flush chamber 28. However, it is preferred that at least the water supply system 66 be pressurized as indicated above. Also, if desired, the chemical wash supply system 70 can be pressurized as well, particularly in the event that the chamber 40 or monitoring chamber 38 is not subatmospheric.

The probe system 36 is shown schematically in FIG. 3 in use in a scrubber recycle system for the removal of combustion products, i.e., gases and wastes, 72 created in a fossil-fueled electrical generating plant so as to prevent their exiting into the environment. In such a plant, it is desirable to remove the solid particulates such as fly ash and to remove or neutralize the $SO_2$ waste gas. These combustion products are admitted into the scrubbing chamber 74 wherein an aqueous solution or slurry stream wets the solid particulates. These particulates become heavy and fall countercurrent to the flow of combustion products through the scrubbing chamber 74 to the bottom where the majority of the particulates is removed for further disposal. The excess aqueous solution is collected along with some residual particulate matter in a reservoir 76 from which it is recycled by a pump 78 back into a monitoring chamber 38 wherein the pH level of the aqueous solution is monitored by the probe system 36. Inside the chamber 38, the solution exits from a nozzle 52 therein which provides a spray 54 of the aqueous solution. A typical recirculation pump 78 is capable of collecting and recirculating approximately 18,000 gallons per minute.

If the aqueous solution available in the reservoir 76 is below a predetermined level, the control unit 22 regulates the admission of fresh water from a liquid supply 80 into the reservoir 76. In addition, the control unit 22 regulates the addition of a chemical additive from a chemical supply 82. The type and amount of chemical added depends on the desired pH level and the type of waste gases which are to be neutralized. In the case of sulfur dioxide ($SO_2$) waste gases, the chemical additive is typically lime or calcium carbonate ($CaCO_3$) which provides a caustic aqueous solution. This in turn requires that the chemical wash from supply system 70 be an acidic solution which is admitted into the flush chamber 28. This is necessary in order to properly neutralize any residual aqueous solution within the chamber 28 and to properly clean the ion sensor cell 16. Preferably, the chemical wash is a 10 percent hydrochloric (HCl) solution taken from a plastic container located at the same level as the probe 10. Since the scrubber operates at a subatmospheric pressure, the HCl solution will flow into the flush chamber 28 when the control unit 22 opens the chemical wash supply system 70. The HCl solution rejuvenates the ion sensor probe 10 by chemically cleaning the ion sensor cell 16 and more particularly the glass surface 20.

In operation, the wash water which removes any deposit of loose buildup on the ion sensor cell 16 is injected every 15 minutes for 15 seconds. Once every 12 hours, the 10% HCl solution is flushed over the ion sensor cell 16 for 20 seconds. If desired, the amount of time during the acid wash can be reduced since the applicant has determined that a period of 5 seconds is sufficient to totally cleans the glass surface 20. Since the amount of wash water and chemical wash is relatively small in comparison to the aqueous solution admitted into the scrubbing chamber 74 the pH level of the aqueous solution is substantially unaffected by these additions.

The probe 10 in probe system 36 as described above is not only self-cleaning but also provides a constant monitoring of the pH level of an aqueous solution or slurry stream. This in turn permits regulation of the amount of chemical additive, i.e., lime or $CaCO_3$, which is necessary to maintain the proper pH level desired. In earlier scrubbing systems, usually the amount of lime or $CaCO_3$ added was more than that necessary to obtain the desired scrubbing operation. Thus the probe system 36 of the present invention provides an economical saving in the amount of lime added which can be closely regulated. In addition, the pH level can be more accurately monitored and thereby maintained, preferably at pH 7.5 or as close to pH 7.0 as is practically possible in the scrubbing system described. This also permits a cost savings in that less lime is necessary to maintain this pH level.

Applicant by means of the present invention has been able to extend the lifetime of ion sensor cells, previously having a typical lifetime of approximately 6 hours, to well over a 100 days, an increased lifetime of over 4,000%. Thus, in addition to providing efficient pH control, the present invention has effectively eliminated the constant replacement of sensor cells and has minimized the maintenance required to a degree not previously attainable. This has been realized in part due to the protection afforded to the ion sensor cells 16 by the enclosure of the lower end of well 42. This enclosure prevents direct contact with the spray 54 and thereby with the solid metallic particles carried by the spray 54. In addition, the enclosure limits the amount and velocity of the spray flow over the sensing portion of the ion sensor cell 16. This in turn reduces the wear and tear on the glass surface 20 of the ion sensor cell 16.

Although the probe system 36 described herein refers to a single ion sensor cell 16 and reference cell 18, applicant's invention is also applicable to a multisensor system and moreover to any system which requires constant pH monitoring of an aqueous solution. In particular, the probe system 36 according to the present invention is applicable to the use of any selective ion cell in a system where the sample to be monitored is a waste solution and the amount of injected acid and water wash solution is not detrimental to the aqueous solution.

I claim:

1. A probe for monitoring the pH of a solution, comprising:
    a. at least one sensor cell having an ion sensor at one end thereof;
    b. housing means defining a chamber for supporting the sensor cell in the chamber, the housing means having an open end permitting entry and exit of at least a portion of the solution, the sensor cell being positioned within the chamber such that the ion sensor is capable of fluid communication with at least a portion of the solution passing through the open end; and
    c. means for cleansing the one end of the sensor cell.

2. A self-cleaning probe for monitoring the pH of a solution, comprising:
    a. at least one ion sensor cell having an ion sensor at one end thereof;
    b. at least one reference cell;
    c. housing means defining a first chamber for supporting the ion sensor cell and the reference cell in the first chamber, the housing means having an open end permitting entry and exit of at least a portion of the solution, the housing means further defining a second chamber communicating with the open end and enclosing the one end of the ion sensor cell, the ion sensor cell being positioned within the second chamber such that the ion sensor is capable of fluid communication with at least a portion of the solution passing through the open end; and
    d. means in communication with the second chamber for passing a cleansing fluid over the one end of the ion sensor cell.

3. The ion sensor probe according to claim 2 wherein the second chamber encloses the ion sensor of the ion sensor cell, the open end of the housing means permitting the ion sensor to come into contact with the solution.

4. The ion sensor probe according to claim 3 wherein the means for passing a cleansing fluid includes means communicating with said second chamber so as to permit passage of the cleansing fluid into and through said second chamber and over the one end of the ion sensor cell.

5. The ion sensor probe according to claim 4 wherein the means for communicating includes a conduit disposed in the housing means, said conduit communicating at one end with said second chamber for passage of the cleansing fluid.

6. The ion sensor probe according to claim 5 wherein said housing means includes:
    a. an elongated hollow member having an opening at one end thereof; and
    b. a plug member having a configuration compatible with the elongated member for insertion into the one end of the elongated member, the plug member having a first passageway for retaining the ion sensor cell and a second passageway for retaining the reference cell, the plug member being configured so as to substantially enclose the ion sensor of the ion sensor cell and thereby define the second chamber.

7. The ion sensor probe according to claim 6 wherein said conduit includes a bore disposed in said plug member.

8. The ion sensor probe according to claim 7 wherein the ion sensor cell and the reference cell are disposed in a side-by-side relationship.

9. The ion sensor probe according to claim 8 wherein the elongated member and plug member are constructed of polyvinylchloride and are generally cylindrical.

10. An ion sensor probe system for monitoring the pH of an aqueous solution in a conduit having an opening at a surface portion thereof, comprising:
    a. at least one ion sensor probe for monitoring the pH of at least a portion of the aqueous solution, said probe including:
        (1) at least one ion sensor cell having an ion sensor at one end thereof;
        (2) housing means including an elongated hollow member having an opening at one end thereof for retaining the ion sensor cell, the ion sensor cell being retained in the housing means so as to have one end available for exposure to the solution, the housing means being configured so as to define a flush chamber substantially enclosing the one end of the ion sensor cell; and (3) means in communication with the flush chamber for cleansing the one end of the ion sensor cell; and b. at least one well member extending through the opening in the conduit and shaped to receive the elongated member therein, the well member at one end extending beyond the one end of the ion sensor cell and defining an enclosure configured so as to permit at least a portion of the solution to contact the one end of the ion sensor cell.

11. The system according to claim 10 wherein said enclosure includes an inlet for admitting at least a portion of the solution into the enclosure and an outlet for discharging the solution within the enclosure, both the inlet and outlet being disposed below the one end of the ion sensor cell, and the inlet being disposed below the outlet.

12. The system according to claim 11 wherein the outlet is smaller in dimension than the inlet so as to provide a pressure buildup of solution entering the enclosure such that the entering solution will substantially fill said enclosure in a spray form and contact the ion sensor cell.

13. The system according to claim 10 further including:

a. means for supplying a first liquid to said flush chamber; and b. means for supplying a second liquid to said flush chamber.

14. The system according to claim 13 wherein the first liquid is substantially water.

15. The system according to claim 13 wherein the second liquid is a chemical solution of at least 10 percent HCl solution.

16. The system according to claim 10 wherein the well member extends through the opening generally transverse of the conduit.

* * * * *